(12) United States Patent
Bischoff (10) Patent No.: US 11,045,221 B2
(45) Date of Patent: Jun. 29, 2021

(54) STEERABLE PERCUTANEOUS PADDLE STIMULATION LEAD

(75) Inventor: Thomas C. Bischoff, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 1725 days.

(21) Appl. No.: 12/905,456

(22) Filed: Oct. 15, 2010

(65) Prior Publication Data

US 2011/0106100 A1 May 5, 2011

Related U.S. Application Data (60) Provisional application No. 61/256,375, filed on Oct. 30, 2009.

(51) Int. Cl.
*A61N 1/05* (2006.01)
*A61B 17/34* (2006.01)
*A61B 17/00* (2006.01)

(52) U.S. Cl.
CPC ........ *A61B 17/3468* (2013.01); *A61N 1/0553* (2013.01); *A61B 2017/003* (2013.01); *A61B 2017/00026* (2013.01); *A61B 2017/00309* (2013.01); *A61B 2017/00314* (2013.01); *A61B 2017/00327* (2013.01); *A61B 2017/00331* (2013.01)

(58) Field of Classification Search
CPC .............. A61B 17/3468; A61B 19/201; A61B 2018/1405; A61B 18/14; A61B 18/1402; A61B 2017/003; A61B 2017/00305; A61B 2017/00309; A61B 2017/00314; A61B 2017/00318–00331; A61B 2017/00336; A61B 1/005; A61B 1/0055; A61B 1/0057; A61B 1/01; A61B 2034/301; A61B 18/1492; A61B 2017/00026; A61N 1/0424; A61N 1/04; A61N 1/044; A61N 1/0488; A61N 1/05; A61N 1/0551; A61N 1/0553; A61N 1/0565; A61N 1/0504
USPC .......... 606/129; 607/116–118; 600/372–374, 600/377–381, 393
See application file for complete search history.

(56) References Cited

U.S. PATENT DOCUMENTS

| | | | | |
|---|---|---|---|---|
| 4,332,259 A | * | 6/1982 | McCorkle, Jr. ............... | 607/123 |
| 4,920,980 A | | 5/1990 | Jackowski | |
| 4,991,603 A | * | 2/1991 | Cohen et al. ................. | 607/125 |
| 5,195,968 A | * | 3/1993 | Lundquist ......... | A61M 25/0144 |
| | | | | 600/585 |

(Continued)

FOREIGN PATENT DOCUMENTS

| | | |
|---|---|---|
| EP | 1818074 | 8/2007 |
| WO | WO08/085528 | 7/2008 |

OTHER PUBLICATIONS

Claeys, L., "Spinal Cord Stimulation and Chronic Critical Limb Ischemia", Neuromodulation, 1999, vol. 2, No. 1.

(Continued)

*Primary Examiner* — Katrina M Stransky
*Assistant Examiner* — Erin L Colello
(74) *Attorney, Agent, or Firm* — Mueting Raasch Group (57) ABSTRACT

The present disclosure relates to a percutaneous paddle stimulation lead that can be steered during implantation. The percutaneous paddle stimulation lead that can be steered in a thickness plane of percutaneous paddle stimulation lead during implantation.

17 Claims, 5 Drawing Sheets

(56) References Cited

U.S. PATENT DOCUMENTS

| | | | |
|---|---|---|---|
| 5,279,299 A * | 1/1994 | Imran | 600/393 |
| 5,396,902 A * | 3/1995 | Brennen et al. | 600/585 |
| 5,501,703 A | 3/1996 | Holsheimer et al. | |
| 5,505,201 A * | 4/1996 | Grill et al. | 600/371 |
| 5,575,814 A * | 11/1996 | Giele et al. | 607/127 |
| 5,643,330 A | 7/1997 | Holsheimer et al. | |
| 5,676,653 A * | 10/1997 | Taylor | A61M 25/0147 604/523 |
| 5,733,322 A * | 3/1998 | Starkebaum | 607/117 |
| 5,800,482 A * | 9/1998 | Pomeranz | A61B 17/00234 606/41 |
| 5,895,416 A * | 4/1999 | Barreras et al. | 607/62 |
| 5,954,761 A * | 9/1999 | Machek et al. | 607/126 |
| 5,967,977 A * | 10/1999 | Mullis et al. | 600/380 |
| 6,038,480 A | 3/2000 | Hrdlicka et al. | |
| 6,106,522 A * | 8/2000 | Fleischman | A61B 5/0422 374/E1.005 |
| 6,112,124 A * | 8/2000 | Loeb | 607/137 |
| 6,192,280 B1 * | 2/2001 | Sommer et al. | 607/122 |
| 6,205,361 B1 * | 3/2001 | Kuzma et al. | 607/116 |
| 6,216,045 B1 * | 4/2001 | Black | A61N 1/05 600/373 |
| 6,236,892 B1 * | 5/2001 | Feler | 607/117 |
| 6,249,707 B1 * | 6/2001 | Kohnen et al. | 607/117 |
| 6,319,241 B1 * | 11/2001 | King et al. | 604/502 |
| 6,374,143 B1 * | 4/2002 | Berrang | A61N 1/0541 600/379 |
| 6,415,187 B1 * | 7/2002 | Kuzma et al. | 607/116 |
| 6,447,506 B1 * | 9/2002 | Swanson et al. | 606/41 |
| 6,512,958 B1 * | 1/2003 | Swoyer et al. | 607/117 |
| 6,522,932 B1 * | 2/2003 | Kuzma et al. | 607/116 |
| 6,587,733 B1 | 7/2003 | Cross, Jr. et al. | |
| 6,721,604 B1 | 4/2004 | Robinson et al. | |
| 6,847,849 B2 * | 1/2005 | Mamo et al. | 607/117 |
| 6,895,276 B2 * | 5/2005 | Kast | A61N 1/3752 439/909 |
| 6,895,283 B2 * | 5/2005 | Erickson et al. | 607/117 |
| 6,909,918 B2 * | 6/2005 | Stypulkowski | 607/117 |
| 7,047,082 B1 | 5/2006 | Schroy et al. | |
| 7,063,682 B1 * | 6/2006 | Whayne | A61B 18/1492 600/146 |
| 7,072,719 B2 * | 7/2006 | Vinup et al. | 607/117 |
| 7,082,335 B2 * | 7/2006 | Klein | A61N 1/0573 607/126 |
| 7,146,224 B2 | 12/2006 | King | |
| 7,184,838 B2 * | 2/2007 | Cross, Jr. | 607/116 |
| 7,191,018 B2 * | 3/2007 | Gielen et al. | 607/129 |
| 7,238,883 B2 * | 7/2007 | Zarembo | A61N 1/056 174/69 |
| 7,241,180 B1 * | 7/2007 | Rentas Torres | A61N 1/05 439/668 |
| 7,319,904 B2 | 1/2008 | Cross, Jr. et al. | |
| 7,359,755 B2 * | 4/2008 | Jones | A61B 17/3415 607/117 |
| 7,396,335 B2 | 7/2008 | Gardeski et al. | |
| 7,437,197 B2 * | 10/2008 | Harris et al. | 607/115 |
| 7,496,410 B2 * | 2/2009 | Heil, Jr. | 607/126 |
| 7,497,844 B2 | 3/2009 | Spear et al. | |
| 7,499,755 B2 | 3/2009 | Cross, Jr. | |
| 7,761,985 B2 * | 7/2010 | Hegland et al. | 29/874 |
| 7,881,809 B2 * | 2/2011 | Rashidi | A61B 18/1492 600/374 |
| 7,894,913 B2 * | 2/2011 | Boggs et al. | 607/118 |
| 7,925,352 B2 * | 4/2011 | Stack et al. | 607/44 |
| 7,949,412 B1 * | 5/2011 | Harrison et al. | 607/137 |
| 8,147,486 B2 * | 4/2012 | Honour et al. | 606/41 |
| 8,380,325 B2 * | 2/2013 | McDonald | 607/119 |
| 8,428,747 B2 * | 4/2013 | Coe | A61N 1/056 607/116 |
| 8,784,336 B2 * | 7/2014 | Bown | A61M 25/0043 600/434 |
| 2001/0018607 A1 * | 8/2001 | Borgersen et al. | 607/121 |
| 2001/0025192 A1 * | 9/2001 | Gerber | A61N 1/0551 607/117 |
| 2002/0022873 A1 * | 2/2002 | Erickson | A61B 5/0422 607/117 |
| 2002/0065544 A1 * | 5/2002 | Smits | A61N 1/0563 607/122 |
| 2002/0128700 A1 * | 9/2002 | Cross, Jr. | 607/117 |
| 2002/0173785 A1 * | 11/2002 | Spear | A61B 18/1492 606/41 |
| 2003/0009095 A1 * | 1/2003 | Skarda | A61B 18/1492 600/374 |
| 2003/0028147 A1 * | 2/2003 | Aves et al. | 604/164.06 |
| 2003/0163171 A1 * | 8/2003 | Kast | A61N 1/3752 607/36 |
| 2003/0204228 A1 * | 10/2003 | Cross et al. | 607/116 |
| 2003/0220677 A1 * | 11/2003 | Doan | A61N 1/056 607/122 |
| 2004/0059404 A1 * | 3/2004 | Bjorklund et al. | 607/126 |
| 2004/0230268 A1 * | 11/2004 | Huff | A61N 1/05 607/116 |
| 2004/0236397 A1 * | 11/2004 | Coe | A61N 1/056 607/116 |
| 2004/0260310 A1 * | 12/2004 | Harris | A61N 1/0553 606/117 |
| 2005/0027338 A1 * | 2/2005 | Hill | A61N 1/05 607/116 |
| 2005/0033393 A1 * | 2/2005 | Daglow | A61B 17/3415 607/116 |
| 2005/0049664 A1 * | 3/2005 | Harris | A61B 17/3401 607/115 |
| 2005/0090885 A1 * | 4/2005 | Harris | A61N 1/0553 607/116 |
| 2005/0182470 A1 * | 8/2005 | Cross, Jr. | 607/117 |
| 2005/0203599 A1 * | 9/2005 | Garabedian et al. | 607/116 |
| 2005/0203600 A1 * | 9/2005 | Wallace | A61N 1/0553 607/116 |
| 2005/0222658 A1 * | 10/2005 | Hoegh et al. | 607/116 |
| 2005/0288759 A1 * | 12/2005 | Jones | A61B 17/3415 607/116 |
| 2006/0089691 A1 * | 4/2006 | Kaplan | A61N 1/056 607/116 |
| 2007/0027514 A1 * | 2/2007 | Gerber | A61N 1/05 607/116 |
| 2007/0038279 A1 * | 2/2007 | Fifer | A61N 1/056 607/116 |
| 2007/0049846 A1 * | 3/2007 | Bown | A61M 25/0043 600/585 |
| 2007/0078455 A1 * | 4/2007 | Rashidi | A61B 18/1492 606/41 |
| 2007/0135803 A1 * | 6/2007 | Belson | 606/1 |
| 2007/0179579 A1 * | 8/2007 | Feler | A61N 1/0553 607/117 |
| 2007/0191709 A1 * | 8/2007 | Swanson | A61N 1/0553 600/433 |
| 2007/0213795 A1 * | 9/2007 | Bradley et al. | 607/116 |
| 2008/0140169 A1 * | 6/2008 | Imran | 607/117 |
| 2008/0147158 A1 * | 6/2008 | Zweber | A61N 1/0534 607/122 |
| 2008/0188917 A1 * | 8/2008 | Gerber | A61N 1/0551 607/117 |
| 2009/0187221 A1 * | 7/2009 | DiGiore et al. | 607/2 |
| 2009/0270960 A1 * | 10/2009 | Zhao | A61N 1/0551 607/117 |
| 2010/0179540 A1 * | 7/2010 | Marczyk | A61B 18/1445 606/41 |

OTHER PUBLICATIONS

Hoisheimer, J., et al., "Clinical Evaluation of Paresthesia Steering with a New System for Spinal Cord Stimulation", Neurosurgery, 1998, No. 3, pp. 541-547.

Holsheimer, J., et al., "Effect of Anode-Chaode Configuration on Paresthesia Coverage in Spinal Cord Stimulation", Neurosurgery, Sep. 1997, pp. 654-659.

(56) References Cited

OTHER PUBLICATIONS

Slavin, K.V., et al., "Efficacy of Transverse Tripolar Stimulation for Relief of Chronic Low Back Pain", Stereotactic and Functional Neurosurgery, 1999, pp. 126-130, vol. 73.

* cited by examiner

STEERABLE PERCUTANEOUS PADDLE STIMULATION LEAD

CROSS-REFERENCE TO RELATED APPLICATIONS

The present application claims priority to U.S. Provisional Patent Application No. 61/256,375, filed Oct. 30, 2009, which application is hereby incorporated by reference as if re-written in its entirety.

BACKGROUND

The medical device industry produces a wide variety of electronic and mechanical devices such as neurological stimulators, therapeutic substance infusion pumps, pacemakers, and defibrillators for treating patient medical conditions such as pain, movement disorders, functional disorders, spasticity, cancer, and cardiac disorders. Medical devices can be configured to be surgically implanted or connected externally to the patient receiving treatment and can be used either alone or in combination with pharmaceutical therapies and surgery to treat patient medical conditions. For certain medical conditions, medical devices provide the best and sometimes the only therapy to restore an individual to a more healthful condition and a fuller life. One type of medical device is an implantable neurological stimulation system typically includes a neurostimulator, an electrical stimulation lead, and an extension. An implantable neurological stimulation system delivers electrical signals to tissue such as neurological tissue or muscle to treat a medical condition.

Electrical stimulation leads can be configured as surgical leads that require an incision for implantation and as percutaneous leads that are implanted through a needle or introducer. Surgical leads are typically less constrained in their shape because the incision used for implantation can be easily varied according to the surgical lead shape. Percutaneous leads are often constrained in their shape because of the requirement to be inserted through a needle or introducer.

A paddle style or flat lead is generally a rectangular shaped flat paddle that is surgically implanted. To introduce a paddle style lead into the epidural space percutaneously using needle insertion, the paddle lead can be rolled to a circular shape to slide through the circular cross section needle. The method of rolling the paddle lead and inserting through a needle and unrolling the paddle style lead has not been perfected for use. Implanting a paddle style lead is accomplished by a surgical procedure known as a laminotomy, a laminectomy, or similar surgical procedure.

BRIEF SUMMARY

The present disclosure relates to a percutaneous paddle stimulation lead. In particular, the present disclosure relates to a percutaneous paddle stimulation lead that can be steered during implantation. In many embodiments the percutaneous paddle stimulation lead that can be steered in a thickness plane of percutaneous paddle stimulation lead during implantation.

In one illustrative embodiment, a percutaneous paddle stimulation lead includes a lead body defining a paddle structure. The lead body has two opposing major surfaces and extends between a proximal end and a distal end. A plurality of electrical contacts disposed on the lead body. A lumen extends through a length of the lead body from the proximal end to the distal end. The lumen is configured to receive a guide wire and allow the lead body to move along the guide wire.

In one illustrative method, a percutaneous paddle stimulation lead is steering by first placing a guidewire into a body. The guidewire extends between a distal end and a proximal end. The distal end is placed in a target area of the body. Then a percutaneous paddle stimulation lead is slid along the guidewire until at least a portion of the percutaneous paddle stimulation lead is placed in the target area of the body. The method then includes removing the guidewire from the body, and the percutaneous paddle stimulation lead remains in the target area of the body.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to a percutaneous paddle stimulation lead. In particular, the present disclosure relates to a percutaneous paddle stimulation lead that can be steered during implantation. In many embodiments the percutaneous paddle stimulation lead that can be steered in a thickness plane of percutaneous paddle stimulation lead during implantation. While the present disclosure is not so limited, an appreciation of various aspects of the disclosure will be gained through a discussion of the examples provided below.

The teachings presented herein are applicable to any implantable medical device system employing lead for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of screening, sensing, monitoring, recording, or the like.

Figure 1:
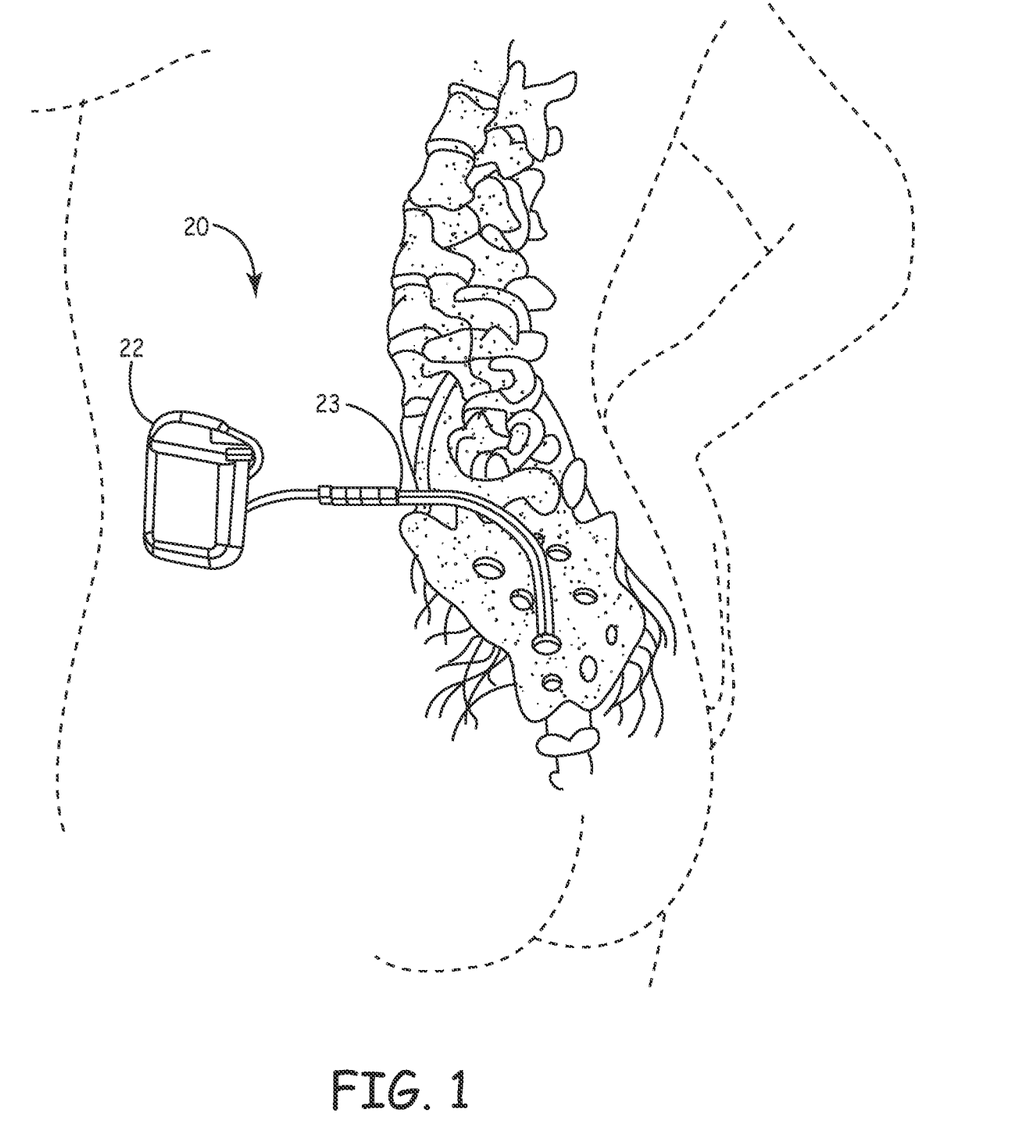
FIG. 1 is a schematic diagram of a neurological lead implanted within a human body or patient.

FIG. 1 shows an environment of an implantable neurological stimulation system 20. The implantable neurological stimulation system 20 includes an implantable neurological stimulator 22, and a stimulation lead 23. The implantable neurological stimulator 22 provides a programmable stimulation signal that is delivered to a desired location or target to stimulate selected nerves or muscle tissue. The implantable neurological stimulator 22 can be implanted in a subcutaneous pocket around the upper buttocks, for example.

The neurological lead 23 is a medical wire with special insulation attached to a planar paddle having a plurality of electrodes (described in more detail below). The neurological paddle leads described herein are designed to be inserted into a patient percutaneously. The neurological lead 23 can be percutaneously implanted and positioned to stimulate a specific site or area of the patient nervous system. The implanted stimulator 22 can be any "active medical device" or "signal generator" as described above and can be placed external to or in any location within a body cavity or tissue within the body, or on the surface of a patient's skin, as desired.

Figure 2A:
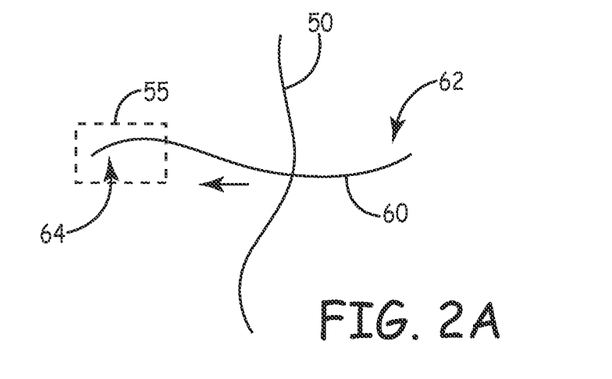
FIG. 2A to FIG. 2C are a schematic diagrams of an illustrative method of steering a percutaneous paddle stimulation lead to a target area in a body.
Figure 2B:
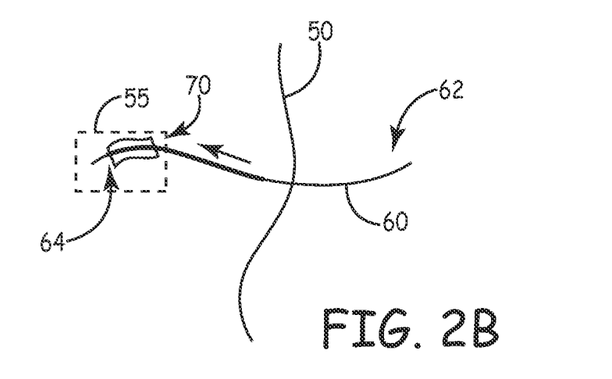
Figure 2C:
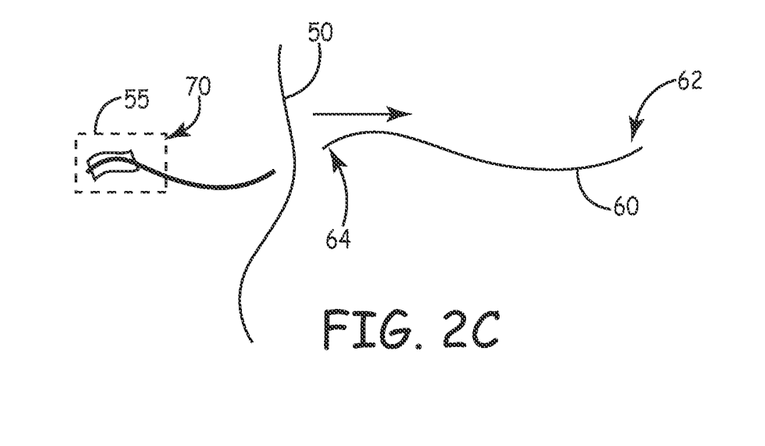

FIG. 2A to FIG. 2C are a schematic diagrams of an illustrative method of steering a percutaneous paddle stimulation lead 70 to a target area 55 in a body 50. FIG. 2A illustrates schematically a guidewire 60 placed into a body 50 I the direction of the arrow. The guidewire 60 extends between a distal end 64 and a proximal end 62. The distal end 64 is placed in a target area 64 of the body 50.

FIG. 2B illustrates schematically sliding a percutaneous paddle stimulation lead 70 along the guidewire 60 until at least a portion of the percutaneous paddle stimulation lead 70 is placed in the target area 55 of the body 50. The percutaneous paddle stimulation lead 70 can be formed of materials that provide enough stiffness to the percutaneous paddle stimulation lead 70 so that the percutaneous paddle stimulation lead 70 can be pushed along the guidewire 60. In other embodiments the percutaneous paddle stimulation lead 70 can be pushed along the guidewire 60 with the assistance of a stylet.

FIG. 2C illustrates schematically removing the guidewire 60 from the body 50. The percutaneous paddle stimulation lead 70 remains in the target area 55 of the body 50. Once the guidewire 60 is removed from the body 50, the percutaneous paddle stimulation lead 70 can be electrically connected to a neurostimulator.

Figure 3A:
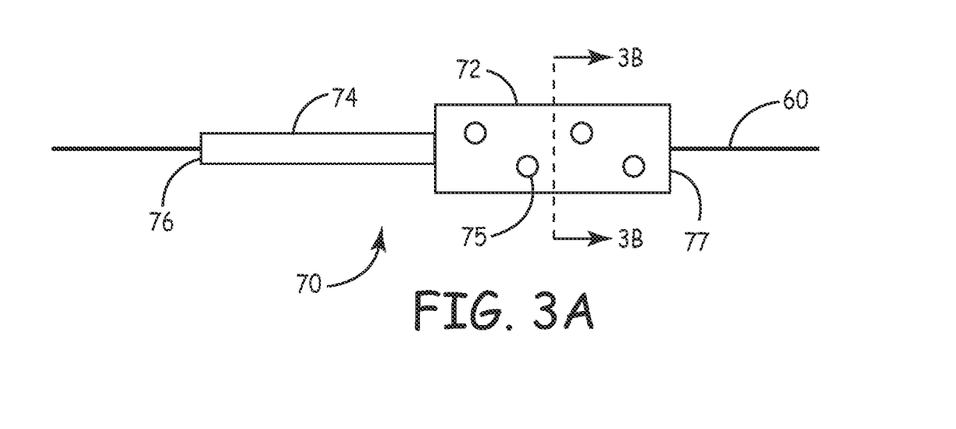
FIG. 3A is a schematic diagram top view of an illustrative percutaneous paddle stimulation lead.
Figure 3B:
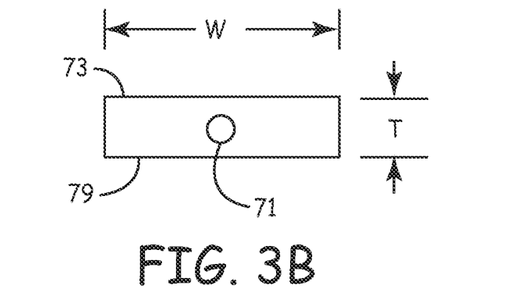
FIG. 3B is a schematic diagram cross-sectional view of the percutaneous paddle stimulation lead of FIG. 3A taken along line 3B-3B.
Figure 3C:
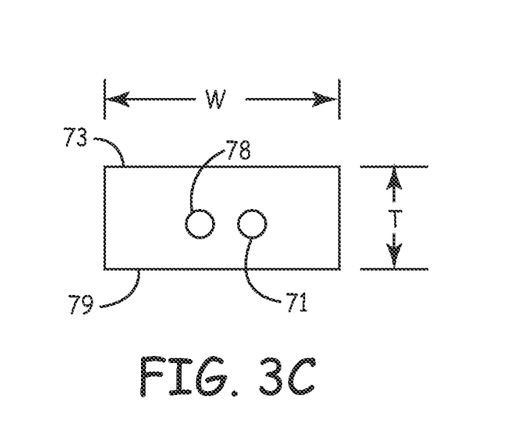
FIG. 3C is a schematic diagram cross-sectional view of another percutaneous paddle stimulation lead embodiment of FIG. 3A taken along line 3B-3B.

FIG. 3A is a schematic diagram top view of an illustrative percutaneous paddle stimulation lead 70. FIG. 3B is a schematic diagram cross-sectional view of the percutaneous paddle stimulation lead 70 of FIG. 3A taken along line 3B-3B. FIG. 3C is a schematic diagram cross-sectional view of another percutaneous paddle stimulation lead embodiment of FIG. 3A taken along line 3B-3B.

The embodiment illustrated in FIG. 3C includes a second lumen 78 that terminates within the percutaneous paddle stimulation lead 70 includes a lead body 74. The second lumen 78 can be configured to receive a stylet (not shown). The stylet can be utilized to "push" the percutaneous paddle stimulation lead 70 along the guidewire 60. Once the percutaneous paddle stimulation lead 70 is placed in the target area, the stylet can be removed from the percutaneous paddle stimulation lead 70.

The percutaneous paddle stimulation lead 70 includes a lead body 74 defining a paddle structure 72. The paddle structure 72 having two opposing major surfaces 73, 79. The lead body 74 extending between a proximal end 76 and a distal end 77. A plurality of electrical contacts 75 are disposed on the lead body 74 paddle structure 72. In many embodiments the electrical contacts 75 are disposed on only one major surface 73 of the two opposing major surfaces 73, 79. While four electrical contacts 75 are illustrated, it is understood that the lead body 74 paddle structure 72 can have any useful number electrical contacts 75 disposed on the lead body 74 paddle structure 72.

A lumen 71 extends through a length of the lead body 74 from the proximal end 76 to the distal end 77. The lumen 71 is configured to receive a guidewire 60 and allow the lead body 74 to move along the guide wire 60. Thus, the guidewire 60 can be placed and the percutaneous paddle stimulation lead 70 is then loaded onto the guidewire 60 and slid along the guidewire 60 in an "over-the-wire" manner.

In many embodiments the lead body paddle structure 72 has a width W value that is greater than a thickness value T of the lead body paddle structure 72. In many embodiments the lead body paddle structure 72 has a width:thickness (W:T) aspect ratio of at least 2:1 or at least 3:1 or at least 4:1 or at least 5:1. The lead body 74 and in particular, the paddle structure 72 is configured to allow the lead body 74 and in particular, the paddle structure 72 to steer within a thickness plane T defined between the two opposing major surfaces 73, 79 of the paddle structure 72. In other words, the paddle structure 72 is configured to allow the lead body 74 and in particular, the paddle structure 72 (having a top surface 73 and an opposing bottom surface 79) to steer in a lateral direction (or side surface direction).

Figure 4A:
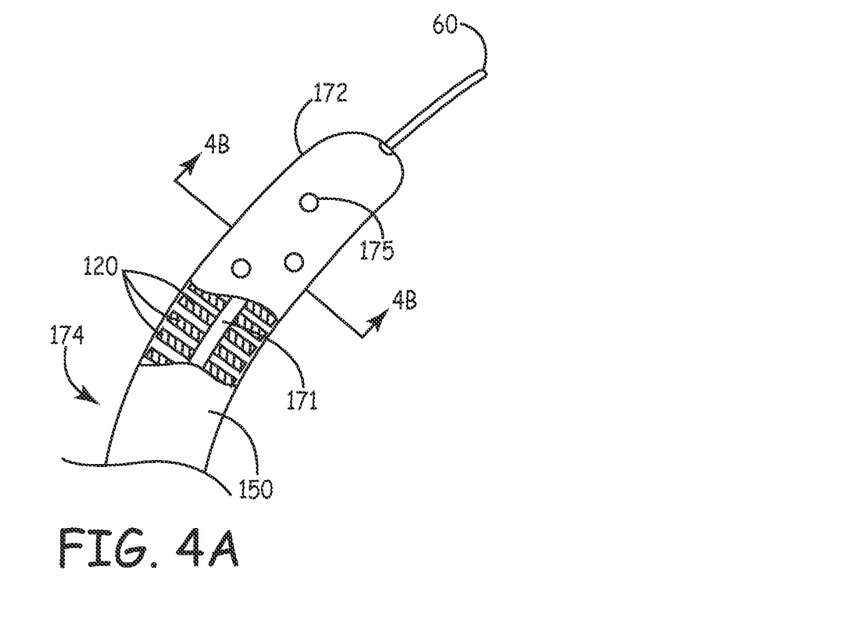
FIG. 4A is a schematic diagram top view of another illustrative percutaneous paddle stimulation lead.
Figure 4B:
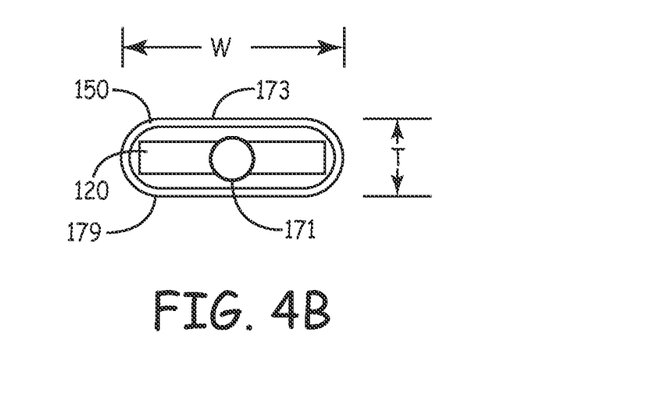
FIG. 4B is a schematic diagram cross-sectional view of the percutaneous paddle stimulation lead of FIG. 4A taken along line 4B-4B.

FIG. 4A is a schematic diagram top view of another illustrative percutaneous paddle stimulation lead. FIG. 4B is a schematic diagram cross-sectional view of the percutaneous paddle stimulation lead of FIG. 4A taken along line 4B-4B.

The percutaneous paddle stimulation lead includes a lead body 174 defining a paddle structure 172. The paddle structure 172 having two opposing major surfaces 173, 179 including a polymeric sheath 150. The lead body 174 extending between a proximal end and a distal end. A plurality of electrical contacts 175 are disposed on the lead body 174 paddle structure 172. In many embodiments the electrical contacts 175 are disposed on only one major surface 173 of the two opposing major surfaces 173, 179. While three electrical contacts 175 are illustrated, it is understood that the lead body 174 paddle structure 172 can have any useful number electrical contacts 175 disposed on the lead body 174 paddle structure 172.

A lumen 171 extends through a length of the lead body 174 from the proximal end to the distal end (as described above). The lumen 171 is configured to receive a guidewire 60 and allow the lead body 174 to move along the guide wire 60. Thus, the guidewire 60 can be placed and the percutaneous paddle stimulation lead is then loaded onto the guidewire 60 and slid along the guidewire 60 in an "over-the-wire" manner.

In many embodiments the lead body paddle structure 172 has a width W value that is greater than a thickness value T of the lead body paddle structure 172. In many embodiments the lead body paddle structure 172 has a width:thickness (W:T) aspect ratio of at least 2:1 or at least 3:1 or at least 4:1 or at least 5:1. The lead body 174 and in particular, the paddle structure 172 is configured to allow the lead body 174 and in particular, the paddle structure 172 to steer within a thickness plane T defined between the two opposing major surfaces 173, 179 of the paddle structure 172.

The paddle structure 172 includes a plurality of fins 120. fins disposed along the length of the lead body 174. The fins 120 are configured to allow the lead body 174 to steer within a thickness plane T defined between the two opposing major surfaces 173, 179 of the paddle structure 172. The fins 120 are separated by lateral spaces to allow the fins to flex and steer the paddle structure 172 within a thickness plane T defined between the two opposing major surfaces 173, 179 of the paddle structure 172.

Figure 5:
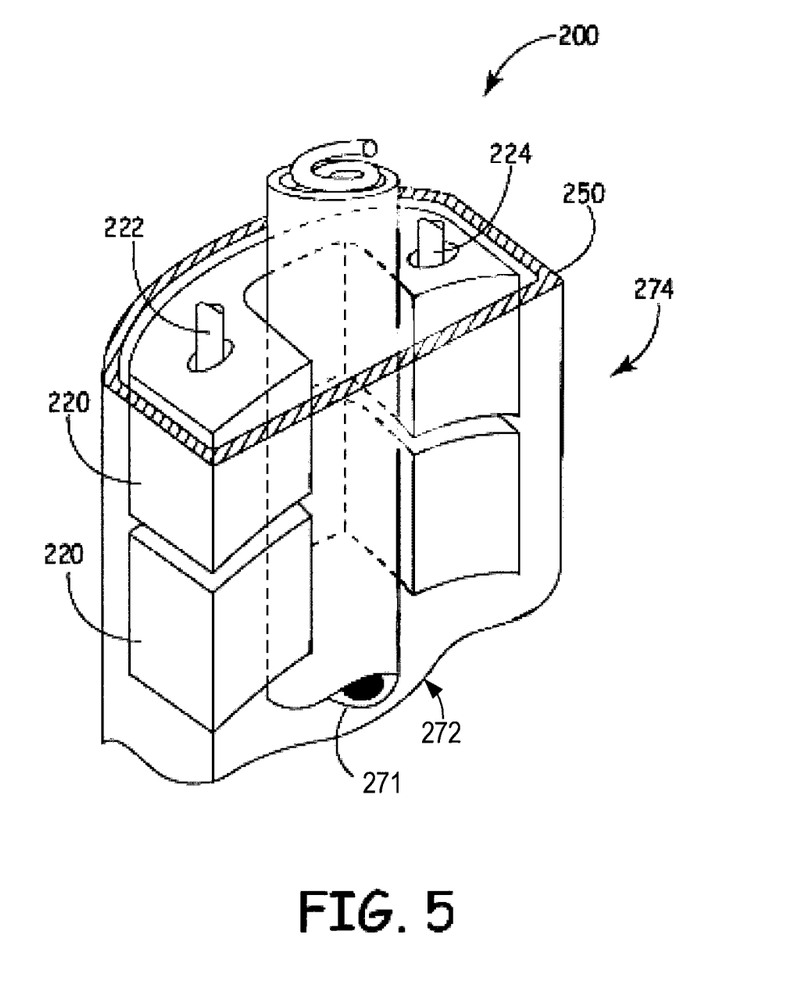
FIG. 5 is a schematic diagram view of another illustrative percutaneous paddle stimulation lead.

FIG. 5 is a schematic diagram view of another illustrative percutaneous paddle stimulation lead 200 including paddle structure 272. This embodiments is similar to the percutaneous paddle stimulation lead shown in FIG. 4A and FIG. 4B except that the lead body 274 is formed of a plurality of stacked segments 220 that are able to move somewhat independently of each other. In many embodiments the plurality of stacked segments 220 are not fixed to one another. A polymeric sheath 250 is disposed about the plurality of stacked segments 220. A lumen 272 is disposed within a notch of each segment 220 and extends along a length of the percutaneous paddle stimulation lead 200. The lumen 272 includes a conductor coil assembly that is electrically connected to electrical contacts on the paddle structure as described above. The lumen 272 can be utilized to receive a guidewire as described above.

A first steering cable 222 and a second steering cable 224 are each extend along a length of the percutaneous paddle stimulation lead 200 and can extend through each of the plurality of stacked segments 220. The lumen 272 can be disposed parallel with and between the first steering cable 222 and the second steering cable 224 as illustrated. The steering cables 222, 224, are fixed to or near a distal end of the percutaneous paddle stimulation lead 200.

When the first steering cable 222 is pulled, the percutaneous paddle stimulation lead 200 is deflected in a first direction that can be within a thickness plane defined between the two opposing major surfaces of the paddle structure, as described above. When the second steering cable 224 is pulled, the percutaneous paddle stimulation lead 200 is deflected in a second direction that can be a direction opposing the first direction and that can be within a thickness plane defined between the two opposing major surfaces of the paddle structure, as described above.

The first and second steering cables 222, 224, can be utilized in all of the percutaneous paddle stimulation leads described herein either in addition to the guidewire or without the guidewire to steer the percutaneous paddle stimulation leads described herein.

Thus, embodiments of the STEERABLE PERCUTANEOUS PADDLE STIMULATION LEAD are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:
1. A percutaneous paddle stimulation lead comprising:
a lead body defining a paddle structure, the lead body having two opposing major surfaces, the lead body extending along a length between a proximal end and a distal end, the lead body having a width:thickness aspect ratio of at least 2:1 throughout the length of the lead body, and the lead body being configured to steer in a lateral direction orthogonal to the thickness and the length;
a plurality of electrical contacts disposed on the lead body; and
a first lumen extending through the length of the lead body from the proximal end to the distal end, the lumen configured receive a guide wire and allow the lead body to move along the guide wire;
wherein the lead body comprises a plurality of fins disposed along the length of the lead body, the fins are configured to allow the lead body to steer in the lateral direction and further wherein lateral spaces extend in between the fins along the length and extend in between the two opposing major surfaces in a thickness direction such that, in a cross-sectional view orthogonal to the length, each lateral space is defined between the two opposing major surfaces, to allow the fins to flex within a thickness plane between the two opposing major surfaces of the lead body.

2. A percutaneous paddle stimulation lead according to claim 1, further comprising a guide wire disposed within the first lumen and extending beyond the proximal end to the distal end of the lead body.

3. A percutaneous paddle stimulation lead according to claim 1, further comprising a polymeric material disposed about the fins and defining the two opposing major surfaces of the paddle structure.

4. A percutaneous paddle stimulation lead according to claim 1, further comprising a polymeric sheath disposed about the fins and defining the two opposing major surfaces of the paddle structure.

5. A percutaneous paddle stimulation lead according to claim 1, wherein the width thickness aspect ratio is at least 3:1.

6. A percutaneous paddle stimulation lead comprising:
a lead body defining a paddle structure, the lead body having two opposing major surfaces, the lead body extending along a length between a proximal end and a distal end, the lead body having a width:thickness aspect ratio of at least 2:1 throughout the length of the lead body, and the lead body being configured to steer in a lateral direction orthogonal to the thickness;
a plurality of electrical contacts disposed on the lead body; and
a first lumen extending through the length of the lead body from the proximal end to the distal end;
wherein the lead body comprises a plurality of adjacent stacked segments that are able to move somewhat independently of each other along the length of the lead body, wherein spaces are defined in between the stacked segments,
wherein the lead body comprises a polymeric sheath defining the two opposing major surfaces of the paddle structure, wherein the spaces are defined in between the two opposing major surfaces such that, in a cross-sectional view orthogonal to the length, each space is defined between the two opposing major surfaces, the polymeric sheath disposed about the stacked segments and the spaces.

7. A percutaneous paddle stimulation lead according to claim 6, wherein the stacked segments are not fixed to one another.

8. A percutaneous paddle stimulation lead according to claim 6, further comprising a first steering cable and a second steering cable extending parallel with the first lumen, wherein the first steering cable can deflect the lead body in a first direction and the second steering cable can deflect the lead body in a second direction opposing the first direction, wherein the first lumen is parallel with the first and second steering cables and is disposed between the first and second steering cables.

9. A percutaneous paddle stimulation lead according to claim 8, wherein the first steering cable and the second steering cable are parallel and extend through the plurality of stacked segments.

10. A percutaneous paddle stimulation lead according to claim 6, wherein the first lumen is configured receive a guide wire and allow the lead body to move along the guide wire.

11. A percutaneous paddle stimulation lead according to claim 6, wherein the width thickness aspect ratio is at least 3:1.

12. A percutaneous paddle stimulation lead comprising:
a lead body defining a paddle structure, the lead body having two opposing major surfaces, the lead body extending along a length between a proximal end and a distal end, the lead body having a width:thickness aspect ratio of at least 2:1 throughout the length of the lead body, and the lead body being configured to steer in a lateral direction orthogonal to the thickness and the length, the lead body further comprising a plurality of stacked segments, a space extending in between each pair of stacked segments along the length, and a polymeric sheath disposed about the stacked segments and the spaces, the polymeric sheath defining the two opposing major surfaces of the paddle structure, wherein the spaces are defined in between the two opposing major surfaces such that, in a cross-sectional view orthogonal to the length, each space is defined between the two opposing major surfaces;
a plurality of electrical contacts disposed on the lead body;
a first steering cable and a second steering cable extending between a proximal end and a distal end of the lead body through the plurality of stacked segments, the first steering cable is fixed near the distal end of the lead body and the second steering cable is fixed near the distal end of the lead body, wherein the first steering cable can deflect the lead body in a first lateral direction and the second steering cable can deflect the lead body in a second lateral direction opposing the first direction; and
a conductor coil assembly disposed within a central lumen extending parallel to the first steering cable and the second steering cable along the length of the lead body, and the conductor coil is disposed between the first steering cable and the second steering cable.

13. A percutaneous paddle stimulation lead according to claim 12, wherein the conductor coil is configured to receive a guidewire and allow the lead body to move along the guidewire.

14. A percutaneous paddle stimulation lead according to claim 12, wherein the plurality of stacked segments are configured to allow the lead body to steer in the lateral direction orthogonal to the thickness.

15. A percutaneous paddle stimulation lead according to claim 12, wherein the lead body comprises a second lumen that terminates within the lead body and is configured to receive a stylet.

16. A percutaneous paddle stimulation lead according to claim 12, wherein the stacked segments are not fixed to one another.

17. A percutaneous paddle stimulation lead according to claim 12, wherein the width thickness aspect ratio is at least 3:1.

* * * * *